(12) United States Patent
Shen et al.

(10) Patent No.: US 10,839,295 B2
(45) Date of Patent: Nov. 17, 2020

(54) METHOD FOR USING DNA TO STORE TEXT INFORMATION, DECODING METHOD THEREFOR AND APPLICATION THEREOF

(71) Applicant: BGI Shenzhen, Shenzhen, Guangdong (CN)

(72) Inventors: Yue Shen, Guangdong (CN); Tai Chen, Guangdong (CN); Longying Liu, Guangdong (CN); Shihong Chen, Guangdong (CN); Yun Wang, Guangdong (CN); Huanming Yang, Guangdong (CN)

(73) Assignee: BGI SHENZHEN, Guangdong (CN)

( * ) Notice: Subject to any disclaimer, the term of this patent is extended or adjusted under 35 U.S.C. 154(b) by 0 days.

(21) Appl. No.: 16/098,471

(22) PCT Filed: May 4, 2016

(86) PCT No.: PCT/CN2016/081037
§ 371 (c)(1),
(2) Date: Nov. 2, 2018

(87) PCT Pub. No.: WO2017/190297
PCT Pub. Date: Nov. 9, 2017

(65) Prior Publication Data
US 2019/0138909 A1    May 9, 2019

(51) Int. Cl.
*G06N 3/12* (2006.01)
*G16B 99/00* (2019.01)
(Continued)

(52) U.S. Cl.
CPC .......... *G06N 3/123* (2013.01); *G06F 40/123* (2020.01); *G06F 40/126* (2020.01);
(Continued)

(58) Field of Classification Search
CPC .... G06N 3/123; C07H 21/04; G06F 17/2205; G06F 17/2217; G06F 17/275; G11C 13/02; G16B 99/00
See application file for complete search history.

(56) References Cited

U.S. PATENT DOCUMENTS

| 2004/0001371 A1* | 1/2004 | Mansuripur | B82Y 10/00 365/200 |
| 2004/0121362 A1* | 6/2004 | Whitney | C07K 14/705 435/6.14 |

(Continued)

FOREIGN PATENT DOCUMENTS

| CN | 1536068 A | 10/2004 |
| CN | 104850760 A | 8/2015 |

(Continued)

OTHER PUBLICATIONS

George M. Church et. al, "Supplementary Materials for Next-Generation Digital Information Storage in DNA", Published Aug. 16, 2012 on Science Express, Retrieved from the Internet <URL:https://science.sciencemag.org/content/sci/suppl/2012/08/15/science.1226355.DC1/Church.SM.pdf > (Year: 2012).*

(Continued)

*Primary Examiner* — Ajay Ojha
(74) *Attorney, Agent, or Firm* — Panitch Schwarze Belisario & Nadel LLP; Stephen G. Small; Lars H. Genieser

(57) ABSTRACT

A method for encoding and storing text information using DNA as a storage medium, a decoding method therefor and an application thereof. The method for using DNA to store text information comprises: encoding characters into computer binary digits by means of encoding, and converting the binary digits into DNA sequences by means of transcoding; and artificially synthesizing the DNA sequences encoded with character information, positioning the characters by (Continued)

means of a designed ligation adapter, and assembling the DNA sequences encoded with the character information according to a pre-set order. The method for using DNA to store text information has the advantages of a small storage volume, a large storage capacity, a strong stability and low maintenance costs.

19 Claims, 4 Drawing Sheets

Specification includes a Sequence Listing.

(51) Int. Cl.
    *G06F 40/123*      (2020.01)
    *G06F 40/126*      (2020.01)
    *G06F 40/263*      (2020.01)
    *G11C 13/02*      (2006.01)

(52) U.S. Cl.
    CPC .......... *G06F 40/263* (2020.01); *G11C 13/02* (2013.01); *G16B 99/00* (2019.02)

(56) References Cited

U.S. PATENT DOCUMENTS

| | | | |
|---|---|---|---|
| 2005/0053968 A1* | 3/2005 | Bharadwaj | B82Y 10/00 |
| | | | 435/6.12 |
| 2008/0057546 A1 | 3/2008 | Lexow | |
| 2014/0315310 A1* | 10/2014 | Lu | G06N 3/002 |
| | | | 435/455 |
| 2017/0141793 A1* | 5/2017 | Strauss | H03M 13/05 |
| 2017/0249345 A1* | 8/2017 | Malik | G06N 3/126 |
| 2017/0335334 A1* | 11/2017 | Lu | C12Q 1/68 |

FOREIGN PATENT DOCUMENTS

| | | |
|---|---|---|
| CN | 105022935 A | 11/2015 |
| CN | 105119717 A | 12/2015 |
| KR | 20160001455 A | 1/2016 |

OTHER PUBLICATIONS

Int'l Search Report and Written Opinion dated Feb. 7, 2017 in Int'l Application No. PCT/CN2016/081037.
Hossein et al., "DNA-Based Storage: Trends and Methods", IEEE Transactions on Molecular, Biological, and Multi-Scale Communications, vol. 1, No. 3, pp. 230-248, Sep. 2015.
O'Driscoll et al., "The next Generation of big data storage", Synthetic DNA, vol. 4, No. 3, pp. 123-125, May 2013.
Gibson et al., "Creation of a Bacterial Cell Controlled by a Chemically Synthesized Genome", Science, vol. 329, No. 5987, pp. 52-56, Jul. 2010.
Gibson "Synthesis of DNA fragments in yeast by one-step assembly of overlapping oligonucleotides", Nucleic Acids Research, vol. 37, No. 20, pp. 6984-6990, Sep. 2009.
Extended European search report dated Feb. 27, 2020 in European Application No. 16900819.0.

* cited by examiner

METHOD FOR USING DNA TO STORE TEXT INFORMATION, DECODING METHOD THEREFOR AND APPLICATION THEREOF

CROSS-REFERENCE TO RELATED APPLICATION

This application is a Section 371 of International Application No. PCT/CN2016/081037, filed May 4, 2016, which was published in the English language on Nov. 9, 2017, under International Publication No. WO 2017/190297 A1, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing", creation date of Nov. 1, 2018, and having a size of about 6.9 kb. The sequence listing submitted via EFS-Web is part of the specification and is herein incorporated by reference in its entirety.

TECHNICAL FIELD

The present invention belongs to the technical field of DNA-based storage, and in particular relates to a method for encoding and storing text information by using DNA as a storage medium, and a decoding method therefor and application thereof.

BACKGROUND

With the development of human society, the accumulated amount of information shows an explosive growth trend. It has been predicted in IDC's report "Digital Universe in 2020" that by 2020 the total amount of global data will exceed 40 ZB! Moreover, the amount of global data is still growing rapidly at a rate of 58% per year, and a large amount of valid data is being lost. Data storage is a problem all over the world. The commonly used storage media at present, such as optical disks and hard disks, have disadvantages such as low storage capacity, large volume, high cost of maintenance and short storage time (~50 years). In order to solve these problems fundamentally, it is necessary to develop a novel information storage medium as soon as possible.

DNA-based storage is a future-focused, subversive information storage technology. The use of DNA as an information storage medium has many advantages such as small volume, large storage capacity, strong stability and low cost of maintenance. Theoretically, 1 gram of DNA can store thousands of terabytes of data, from which it is estimated that the storage of all the existing information of human beings including books, files, videos, etc. can be achieved by using only hundreds of kilograms of DNA, and the storage time can be up to thousands of years under normal conditions. Therefore, those information that is not commonly used but needs long-term preservation, such as government documents and historical files, etc., is especially suitable for DNA-based storage.

Although DNA-based storage has many superior advantages as compared with the existing storage, there are some technical barriers that hinder its development, such as the inability to reuse synthetic DNA oligo fragments, high cost of DNA synthesis, complex design and poor flexibility, etc., resulting in difficulties in large-scale promotion and application of the existing DNA-based storage technology. Therefore, it is necessary to start from the design of basic information-constituting unit to optimize the coding design of DNA-based storage, thereby reducing costs and improving efficiency and convenience.

SUMMARY OF THE INVENTION

It is an object of the present invention to provide a method for encoding and storing text information by using DNA as a storage medium, and a decoding method therefor and application thereof.

The method for storing text information provided by the present invention generally comprises: firstly, encoding a character into a computer binary digit by encoding, and then converting the binary digit into a DNA sequence by transcoding; and secondly, artificially synthesizing the DNA sequence encoding the character information and locating the character by a designed ligation adapter to assemble the DNA sequences encoding the characters in a preset order. Alternatively, the assembled DNA sequences can be further assembled into a longer DNA sequence as needed.

In the method for storing text information of the present invention, each character can be used repeatedly, and by changing the adapter, can be used for storing any information, the principle of which is the same as that of the "movable-type printing" strategy. The DNA which has stored text information can be preserved under appropriate conditions. When the stored information needs to be read, the stored character information can be obtained by sequencing the DNA sequence followed by decoding with a computer (as shown in FIG. 1). The method provided by the present invention has the advantages of small storage volume, large storage capacity, strong stability and low cost of maintenance, etc by using DNA as a storage medium.

Specifically, the technical object of the present invention can be achieved by the following aspects:

In a first aspect, the present invention provides a method for storing text information by using DNA as a storage medium, comprising the steps of:

(1) encoding a character into a computer binary digit by encoding;

(2) converting the computer binary digit encoding the character into a DNA sequence, which is represented by the four deoxyribonucleotides A, T, G, and C, by transcoding;

(3) synthesizing the DNA sequence encoding the character;

(4) locating the DNA sequence encoding the character by a designed ligation adapter, assembling individual DNA sequences encoding individual characters according to the order of characters of the information to be stored, followed by storing.

Regarding Encoding

In an alternative particular embodiment, the encoding is Unicode-ucs2 encoding; that is, each Chinese character is encoded by a hexadecimal digit, for example, the corresponding Unicode code of the character "唵" is U+5535; each 1-bit hexadecimal digit is converted into a 4-bit binary digit, for example, 5 is converted into 0101 and 3 is converted into 0011, and thus the character "唵" is converted into a binary digit 0101010100110101; preferably, each 8-bit binary digit produce a 4-bit Hamming code for verification, and thus the Hamming codes of the character "

唵" are 0010 and 1110 respectively. Finally, a complete binary code of the character "唵" can be obtained, that is 010101010010001101011110.

Regarding Transcoding

In an optional particular embodiment, the transcoding is performed according to the principle that the binary digit 0 is converted into G or T and the binary digit 1 is converted into C or A so as to convert the binary digit encoding a character into a DNA sequence.

Preferably, one Chinese character is encoded into 24 bases.

Preferably, the sequence design is controlled by considering one or more of parameters including GC content, secondary structure and base repetition rate of the DNA sequence; for example, preferably, the DNA sequence is designed such that the GC content thereof is 45-60%, preferably 50%; preferably, the DNA sequence is designed to avoid the formation of secondary structure; preferably, the DNA sequence is designed such that no more than 2 consecutive single bases are present therein. Taking the character "唵" as an example, it is finally converted into a DNA sequence TAGCTATAGGCTTGCATAGCACCG.

Regarding the DNA Sequence and the Ligation Adapter

Both the DNA sequence and the ligation adapter sequence in the present invention are obtained by de novo chemically synthesizing the forward and reverse strands and allowing them to anneal to form a double-stranded structure.

In an optional particular embodiment, a complementary locating base protrudes from both the DNA sequence fragment and the ligation adapter. The directional ligation of the DNA sequence to the ligation adapter is achieved via the complementary bases (i.e., "locating base") respectively protruding from the DNA sequence and the ligation adapter. By designing the ligation adapter, DNA sequence fragments encoding various characters can be ligated in the desired character order.

In an optional particular embodiment, the ligation adapter comprises an upstream adapter and a downstream adapter; ligation adapters with the same DNA sequence but the different overhanging locating bases will linked to the upstream and downstream of two DNA fragments respectively, and the resulted two DNA fragments can be ligated by the ligation adapters by using a conventional molecular biology method, preferably by PCA, GoldenGate, etc. (as shown in FIG. 2).

For example, one base protrudes from each end of a DNA fragment respectively, such as a base "A" protrudes from the sense strand and a base "G" protrudes from the antisense strand of the DNA fragment at 5'-end, in which case, a base "T" should protrude from the antisense strand of the corresponding upstream adapter and a base "C" should protrude from the sense strand of the downstream adapter such that the directional ligation of the fragment to the adapter can be achieved by means of A/T and G/C pairing, that is, the adapter overhanging a "T" can only be linked at upstream of the DNA fragment and the adapter overhanging a "C" can only be linked at downstream of the DNA fragment. Similarly, the bases protruding from upstream and downstream of a DNA fragment may also be A/C, T/G and T/C, etc., in which case the corresponding bases protruding from the adapter become T/G, A/C and A/G, etc., correspondingly (as shown in FIG. 3A). Similarly, more than one unpaired base may protrude from each of the DNA fragment and the adapter. Similarly, the base may protrude from the DNA fragment and the adapter at the 3'-end thereof. A base "G" may protrude from the sense strand of the DNA fragment at both 5'-end and 3'-end, in which case, a base "C" should protrude from the antisense strand of the corresponding upstream adapter at 5'-end and the antisense strand of the downstream adapter at 3'-end, also allowing the directional ligation of the fragment to the adapter. Similarly, the bases protruding from the sense strand of a DNA fragment at 5'-end and 3'-end may also be "C", "T" or "A", in which case the bases protruding from the adapter should become "G", "A" or "T", correspondingly. Similarly, "G", "C", "T" or "A" may protrude from the antisense strand of a DNA fragment, in which case "C", "G", "A" or "T" should protrude from the sense strand of the adapter, correspondingly (as shown in FIG. 3B). Similarly, more than one complementary base may protrude from each of the DNA fragment and the adapter.

Sequence of the ligation adapter can be automatically generated by a computer program. For example, a PCA adapter needs to have a length of more than 8 bp, a GC content of 50%-60%, no secondary structure, no more than 2 consecutive bases, and no mismatch between the same set of adapters, etc.; a GoldenGate adapter consists of an enzymatic cleavage site sequence and its outer protective bases, and the difference in the 4 bp sticky ends resulting from enzyme restriction between the same set of adapters needs to be more than 2 bp (as shown in FIG. 3C). The 5'-ends of the sense and antisense strands of the DNA fragment, the antisense strand of the upstream adapter, and the sense stand of the downstream adapter are phosphorylated. The 5'-ends of the sense strand of the upstream adapter and the antisense strand of the downstream adapter are dephosphorylated to reduce the probability of self-linking and misligation of the adapters.

For the Assembly and Preservation

To the DNA sequences encoding the characters are respectively added the designed ligation adapters, though which locating is achieved; in a particular embodiment, by overlap extension PCR, individual DNA sequences comprising the encoding information of individual characters are ligated according to the character order of the information to be stored, and the ligated sequences can be further assembled into a longer DNA sequence; preferably, individual DNA sequences comprising the encoding information of individual characters are ligated by a method such as PCA or GoldenGate; preferably, the ligated DNA sequences are assembled by a Gibson method and the assembled DNA sequence which encodes the character information can be preserved under suitable storage conditions, for example, can be lyophilized for long-term storage at low temperatures.

In a particular embodiment, characters may be firstly assembled into a form of phrase or idiom, etc., such that the subsequent assembly becomes more convenient and efficient; for example, 10-20 characters may be assembled into a short sentence at once by using a method such as PCA or GoldenGate, etc., and then the short sentences can be further spliced into a long sentence, a paragraph or an article by using an assembly method such as Gibson assembly, etc.

Preferably, the assembled DNA sequence is cloned into a plasmid for storage; preferably, a step of verifying the correctness of the assembled DNA sequence by sequencing is also included prior to the storage.

In a second aspect, the present invention also provides a method for decoding the text information stored according to the method of the first aspect, comprising the steps of:

(1) sequencing the DNA sequence which stores text information, for example, by sanger sequencing, second generation sequencing, third generation sequencing or other sequencing methods;

(2) converting the sequenced DNA sequence into a binary digit, which in turn is converted into a corresponding Chinese character according to the same transcoding and encoding rules as defined in the method described in the first aspect to obtain the stored text information.

When a mutation exists in the DNA sequence, it can be corrected by the Hamming code. For example, if the base at position 2 of the above DNA sequence is mutated from A to G, i.e. the DNA sequence becomes TGGCTATAGGCTTG-CATAGCACCG, the corresponding binary digit will become 000101010010001101011110. It can be calculated according to the Hamming code verification principle that the base at position 2 is mutated, and thereby the binary digit will be corrected to 010101010010001101011110 and the sequence can still be correctly decoded as "唵".

Therefore, in particular embodiments, the decoding may further include the step of correcting mutations in the DNA sequence according to the Hamming code verification principle.

In a third aspect, the present invention provides use of the method for storing text information according to the first aspect and/or the method for decoding the stored text information according to the second aspect in the storage and/or reading of text information.

Beneficial Effects

First, the method for storing text information according to the present invention has the advantages of small storage volume, large storage capacity, strong stability and low cost of maintenance, etc. by using DNA as a storage medium.

In addition, compared with other existing DNA storage methods, the present method is more suitable for storing text information, supporting text forms including characters of various countries including all Chinese characters, English letters, Japanese and Korean, etc., punctuation marks and mathematical symbols, etc.; has high encoding efficiency, wherein 1000 Chinese characters can be encoded within 100 milliseconds; adopts a strategy similar to "movable-type printing", wherein the DNA fragments and adapters can be used repeatedly, resulting in lower cost of synthesis; the stored DNA sequence can be in a double-stranded closed circular conformation, which is more stable in storage; the stored DNA sequence can be verified by sequencing and the Hamming verification code can be added thereto, allowing any one mutation in every 12 bases, which results in a more fidelity; and the stored DNA sequence is a long double-stranded DNA, which is more easier for reading information.

DETAILED DESCRIPTION

The experimental procedures described in the following examples are only used to demonstrate the feasibility of the method of the patent, and the application of the method of the invention is not limited thereto.

The experimental procedures mentioned in the examples are conventional experimental methods unless otherwise specified; the reagents and consumables mentioned are conventional reagents and consumables unless otherwise specified. The synthetic oligos used in the experiments were diluted to 100 µM and the primers were diluted to 10 µM with sterile water.

Example 1 Assembly Test

The phrase for the assembly test: 华章谱写基因梦.

Transcoding was performed according to the method of the present invention and DNA oligo sequences were synthesized; the PCA adapters were used for locating and ligating according to G/C and A/T base pairing manner at the upstream and downstream, respectively. The DNA oligo and primer sequences were shown in Table 1 below.

1. Annealing

The forward and reverse oligos were each taken 10 µL for each character or adapter, mixed and annealed; the annealing procedure was: denatured at 99° C. for 10 min, slowly cooled to 25° C. at 0.1° C./sec, maintained at 12° C.

2. Ligation

To each character were added upstream and downstream adapters in order respectively for ligation; the ligation system was: 1 µL of T4 DNA ligase (Enzymatics), 10 µL of 2×ligation buffer, 2 µL each of the annealed character, upstream adapter and downstream adapter, 3 µL of ddH$_2$O; ligating at 16° C. overnight.

3. Purification of the Ligation Product

Figure 1:
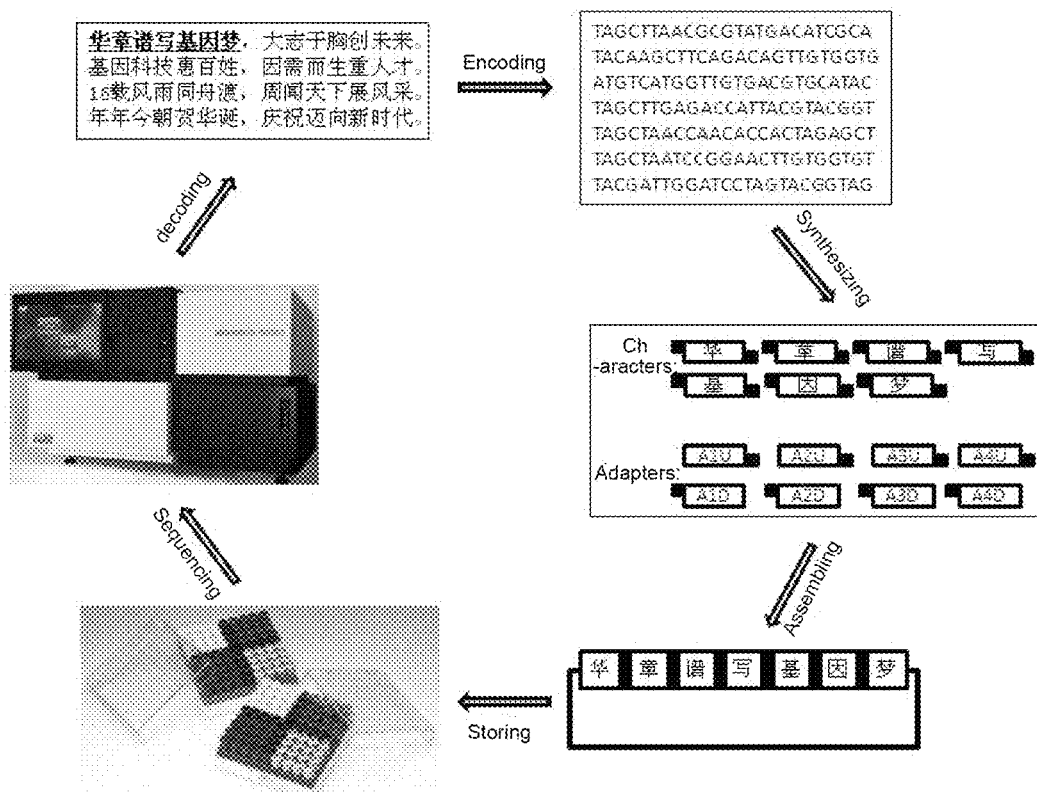
FIG. 1 shows a schematic view showing the overall flow of Example 1 of the present invention.
Figure 2:
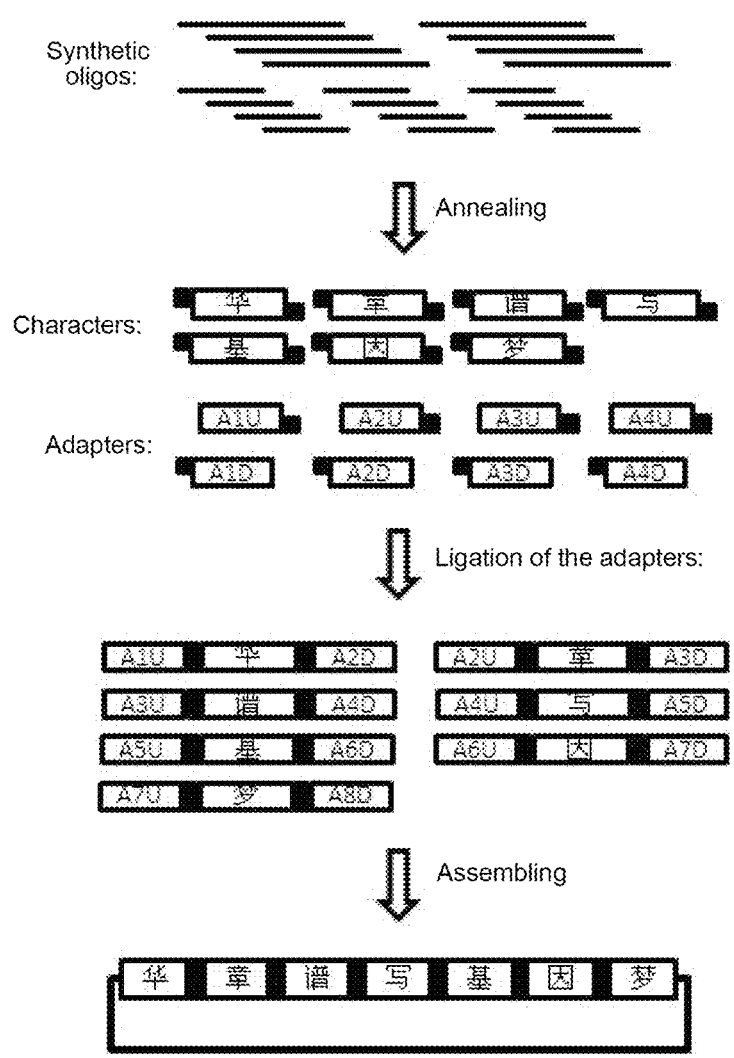
FIG. 2 shows a schematic view showing the assembly flow of Example 1 of the present invention.
Figure 3:
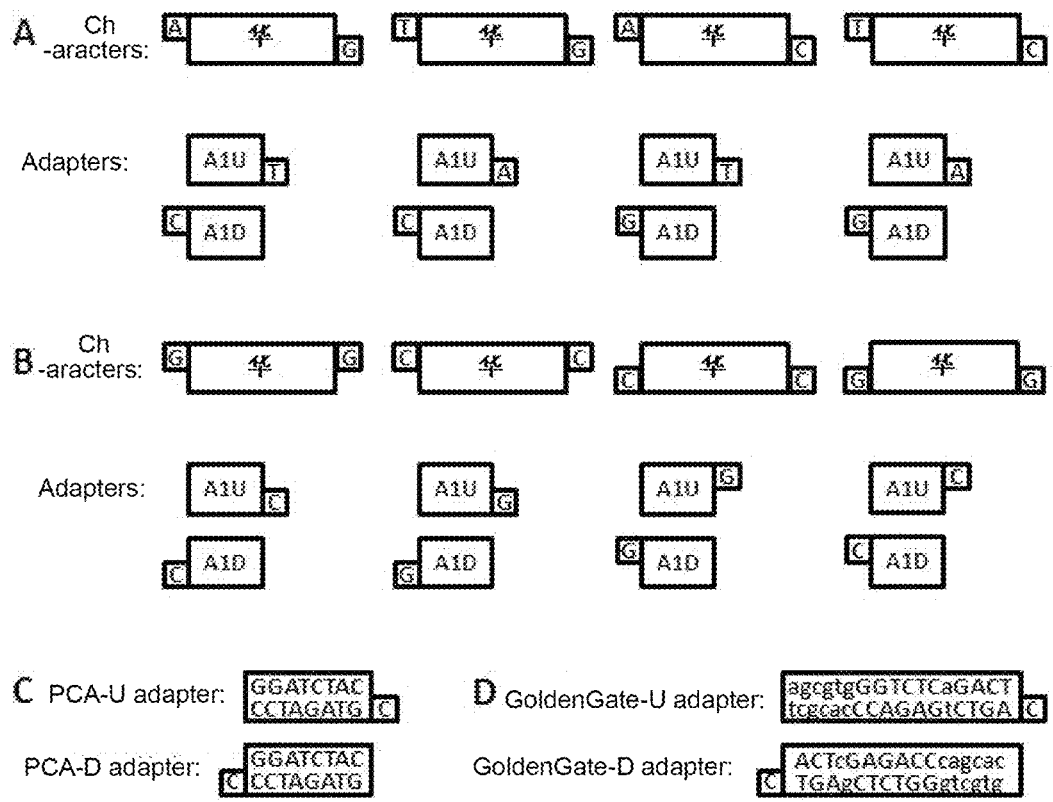
FIG. 3 shows schematic views showing the designs of fragments/adapters of Example 1 of the present invention.
Figure 4:
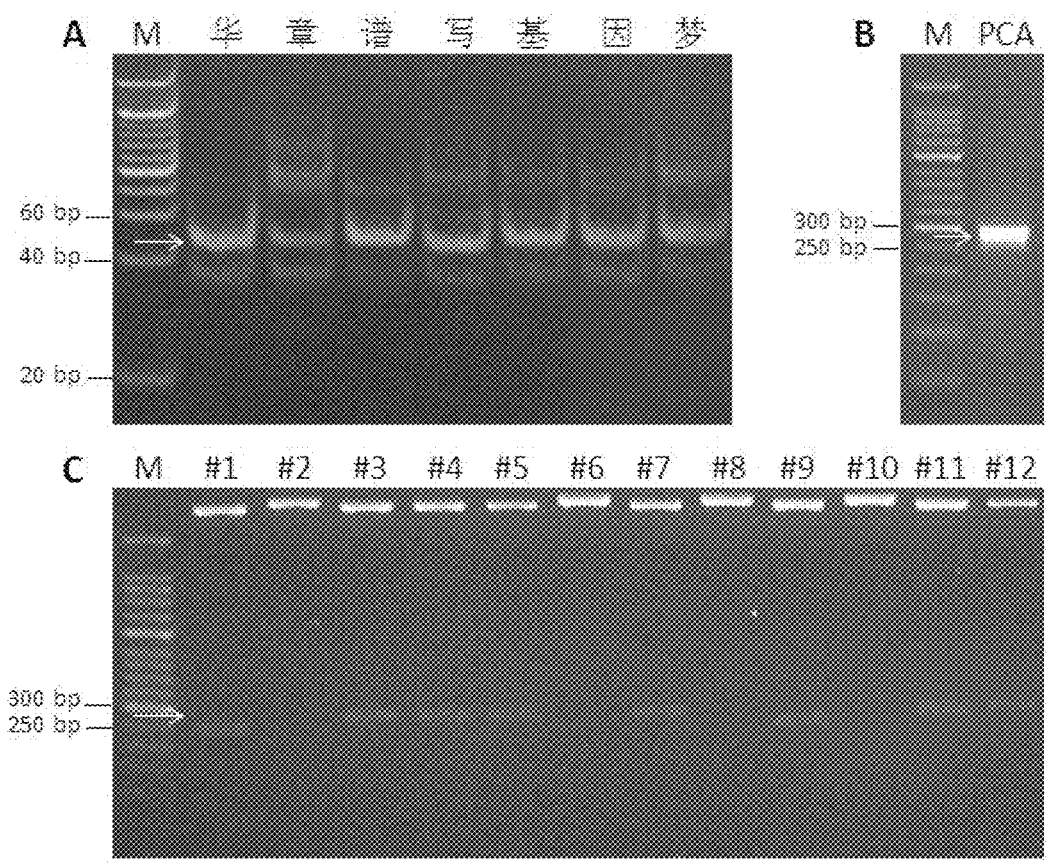
FIG. 4 shows electrophoretograms of the assembly test results of Example 1 of the present invention.

The ligation products were subjected to gel electrophoresis on 15% PAGE gel at 100 V for 1 h (the electrophoresis results were shown in FIG. 4A); the target bands (42 bp in size, as indicated by the arrow in FIG. 4A) were cut off and purified: the cut gel was placed into a 0.5 mL tube with punctured bottom, which was then placed into a 2 mL tube, centrifuged at 14,000 rpm for 2 min, 200 µL of 0.3 M NaCl was added to the broken gel, shaken at 1400 rpm at 25° C. for 2 h; the broken gel and the liquid were transferred together into a filter column, centrifuged at 14,000 rpm for 2 min, the filtrate was transferred into a 1.5 mL centrifuge tube, 400 µL of absolute ethanol was added, left for sinking at −80° C. for 1 h. Centrifuged at 14000 rpm at 4° C. for 30 min, discarded the supernatant, 500 µL of 70% ethanol was added for washing the precipitate once, drawn off the supernatant, dried at 37° C. for 5 min, and 20 µL of ddH$_2$O was added to dissolve the DNA.

4. Assembly

The characters were assembled into a short sentence by using a method of PCA. Step 1: 0.2 µL of Ex Taq DNA polymerase (TAKARA), 2 µL of 10×buffer, 1.6 µL of 2.5 mM dNTPs, 50 ng each of the ligated, cut and purified products of adapter1-U+华+adapter2-D, adapter2-U+章+adapter5-D, adapter5-U+谱+adapter6-D, adapter6-U+写+adapter7-D, adapter7-U+基+adapter8-D, adapter8-U+因 adapter9-D and adapter9-U+梦+adapter10-D, adding water to 20 µL. 94° C. for 5 min; 94° C. for 30 sec, 55° C. for 1 sec, cooled to 45° C. at 0.5° C./sec, 45° C. for 15 sec, 72° C. for 1 min, 20 cycles; 72° C. for 5 min, maintained at 12° C. Step 2: 0.2 µL of Ex Taq DNA polymerase (TAKARA), 2 µL of 10×buffer, 1.6 µL of 2.5 mM dNTPs, 3 µL of the PCR product of step 1, 1 µL each of the primers 12-F and St1-R, 11.2 µL of ddH$_2$O. 94° C. for 5 min; 94° C. for 30 sec, 60° C. for 30 sec, 72° C. for 30 sec, 35 cycles, 72° C. for 5 min, maintained at 12° C.

The PCR product was detected by electrophoresis: 5 μL of PCR product was used for electrophoresis detection. The electrophoresis was performed with 2% agarose gel at 180 V for 30 min (The electrophoresis result was shown in FIG. 4B. The PCR product was approximately 280 bp in size as indicated by the arrows).

5. TA Cloning

The PCR product obtained in step 4 was purified by gel purification with a gel purification kit and the purified PCR product was cloned with a TA cloning kit (TAKARA).

6. Identification by Restriction Digestion

Monoclones were selected from the TA cloning plate obtained in step 5, incubated overnight, followed by plasmid extraction with a kit and identification by restriction digestion with the designed BssHII restriction site. The digestion system was: 0.5 μL of BssHII (NEB), 1 μL of CutSmart buffer, 4 μL of plasmid DNA and 4.5 μL of ddH$_2$O. Digested at 37° C. for 1 h. 5 μL of the digested product was used for electrophoresis with 2% agarose gel at 180 V for 30 min (the electrophoresis results were shown in FIG. 4C and the band with correct size was indicated by the arrow).

7. Sequencing Analysis

The correctly enzyme-digested plasmid was selected for sanger sequencing, and the plasmid with the correct assembly sequence was analyzed and obtained.

TABLE 1

| NO. | Sequence |
|---|---|
| 华-F (SEQ ID NO. 1) | ATAGCTTAACGCGTATGACATCGCA |
| 华-R (SEQ ID NO. 2) | GTGCGATGTCATACGCGTTAAGCTA |
| 章-F (SEQ ID NO. 3) | ATACAAGCTTCAGACAGTTGTGGTG |
| 章-R (SEQ ID NO. 4) | GCACCACAACTGTCTGAAGCTTGTA |
| 谱-F (SEQ ID NO. 5) | AATGTCATGGTTGTGACGTGCATAC |
| 谱-R (SEQ ID NO. 6) | GGTATGCACGTCACAACCATGACAT |
| 写-F (SEQ ID NO. 7) | ATAGCTTGAGACCATTACGTACGGT |
| 写-R (SEQ ID NO. 8) | GACCGTACGTAATGGTCTCAAGCTA |
| 基-F (SEQ ID NO. 9) | ATAGCTAACCAACACCACTAGAGCT |
| 基-R (SEQ ID NO. 10) | GAGCTCTAGTGGTGTTGGTTAGCTA |
| 因-F (SEQ ID NO. 11) | ATAGCTAATCCGGAACTTGTGGTGT |
| 因-R (SEQ ID NO. 12) | GACACCACAAGTTCCGGATTAGCTA |
| 梦-F (SEQ ID NO. 13) | ATACGATTGGATCCTAGTACGGTAG |
| 梦-R (SEQ ID NO. 14) | GCTACCGTACTAGGATCCAATCGTA |

TABLE 1-continued

| NO. | Sequence |
|---|---|
| adapter1-UF (SEQ ID NO. 15) | CTCATTCC |
| adapter1-UR (SEQ ID NO. 16) | TGGAATGAG |
| adapter2-UF (SEQ ID NO. 17) | AATTCGCG |
| adapter2-UR (SEQ ID NO. 18) | TCGCGAATT |
| adapter2-DF (SEQ ID NO. 19) | CAATTCGCG |
| adapter2-DR (SEQ ID NO. 20) | CGCGAATT |
| adapter5-UF (SEQ ID NO. 21) | CCTTTAGC |
| adapter5-UR (SEQ ID NO. 22) | TGCTAAAGG |
| adapter5-DF (SEQ ID NO. 23) | CCCTTTAGC |
| adapter5-DR (SEQ ID NO. 24) | GCTAAAGG |
| adapter6-UF (SEQ ID NO. 25) | ACAGAGAC |
| adapter6-UR (SEQ ID NO. 26) | TGTCTCTGT |
| adapter6-DF (SEQ ID NO. 27) | CACAGAGAC |
| adapter6-DR (SEQ ID NO. 28) | GTCTCTGT |
| adapter7-UF (SEQ ID NO. 29) | CCGTCATA |
| adapter7-UR (SEQ ID NO. 30) | TTATGACGG |
| adapter7-DF (SEQ ID NO. 31) | CCCGTCATA |
| adapter7-DR (SEQ ID NO. 32) | TATGACGG |
| adapter8-UF (SEQ ID NO. 33) | GGATCTAC |
| adapter8-UR (SEQ ID NO. 34) | TGTAGATCC |
| adapter8-DF (SEQ ID NO. 35) | CGGATCTAC |
| adapter8-DR (SEQ ID NO. 36) | GTAGATCC |
| adapter9-UF (SEQ ID NO. 37) | GTTGCATC |
| adapter9-UR (SEQ ID NO. 38) | TGATGCAAC |
| adapter9-DF (SEQ ID NO. 39) | CGTTGCATC |
| adapter9-DR (SEQ ID NO. 40) | GATGCAAC |

TABLE 1-continued

| NO. | Sequence |
|---|---|
| adapter10-DF (SEQ ID NO. 41) | CATCGGGAA |
| adapter10-DR (SEQ ID NO. 42) | TTCCCGAT |
| St12-F (SEQ ID NO. 43) | GCGCGCTTGGTTCAGACGTGAGAAGTGATGCA CAGTAGCTTAACGCGTATGACATCGCA |
| St1-R (SEQ ID NO. 44) | GCGCGCTACCGTACTAGGATCCAATCG |

The Applicant states that the method and application thereof of the present invention are illustrated through the above examples, however, the present invention is not limited thereto. Those skilled in the art should understand that, for any improvement of the present invention, the equivalent replacement of the products of the present invention, the addition of auxiliary components, and the selection of specific modes, etc., will all fall within the protection scope and the disclosure scope of the present invention.

The invention claimed is:

1. A method for storing text information by using DNA as a storage medium, comprising the steps of:
   (1) encoding a character into a computer binary digit by encoding;
   (2) converting the computer binary digit encoding the character into a DNA sequence, which is represented by the four deoxyribonucleotides A, T, G, and C, by transcoding;
   (3) synthesizing the DNA sequence encoding the character;
   (4) locating the DNA sequence encoding the character by a designed ligation adapter, ligating individual DNA sequences encoding individual characters according to the order of characters of the information to be stored, followed by assembling and storing;
   wherein the DNA sequence is designed to avoid the formation of secondary structure.

2. The method according to claim 1, wherein the encoding is Unicode-ucs2 encoding.

3. The method according to claim 2, wherein the character is a Chinese character, and wherein the Chinese character is encoded by a hexadecimal digit, and the hexadecimal digit is converted into a 4-bit binary digit.

4. The method according to claim 3, wherein the 8-bit binary digit produces a 4-bit Hamming code for verification.

5. The method according to claim 1, wherein the transcoding is performed according to a principle that the binary digit 0 is converted into G or T and the binary digit 1 is converted into C or A so as to convert the binary digit encoding a character into a DNA sequence.

6. The method according to claim 1, wherein the character is a Chinese character, and the Chinese character is encoded into 24 bases.

7. The method according to claim 1, wherein the sequence design is controlled by considering one or more of parameters selected from the group consisting of GC content and base repetition rate of the DNA sequence.

8. The method according to claim 7, wherein the DNA sequence is designed such that the GC content thereof is 45-60%.

9. The method according to claim 7, wherein the DNA sequence is designed such that the GC content thereof is 50%.

10. The method according to claim 7, wherein the DNA sequence is designed such that no more than 2 consecutive single bases are present therein.

11. The method according to claim 1, wherein the ligation adapter in step (4) comprises an upstream adapter and a downstream adapter.

12. The method according to claim 1, wherein the directional ligation of the DNA sequence to the ligation adapter is achieved via the complementary bases respectively protruding from the DNA sequence and the ligation adapter.

13. The method according to claim 1, wherein by overlap extension PCR, individual DNA sequences comprising the encoding information of individual characters are ligated, followed by being further assembled into a longer DNA sequence.

14. The method according to claim 1, wherein the ligation is performed by PCA or GoldenGate method.

15. The method according to claim 1, wherein the assembly is performed by Gibson method.

16. The method according to claim 1, wherein the assembled DNA sequence is cloned into a plasmid for storage.

17. The method according to claim 1, wherein a step of verifying the correctness of the assembled DNA sequence by sequencing is further included prior to the storage.

18. A method for decoding the text information stored according to the method of claim 1, comprising the steps of:
   (1) sequencing the DNA sequence which stores text information;
   (2) converting the sequenced DNA sequence into a binary digit, which in turn is converted into a corresponding Chinese character according to the same transcoding and encoding rules as defined in the method according to claim 1 to obtain the stored text information.

19. The method according to claim 18, wherein the decoding process further comprises correcting mutations in the DNA sequence according to the Hamming code verification principle.

* * * * *

SEQUENCE LISTING

```
<160> NUMBER OF SEQ ID NOS: 44

<210> SEQ ID NO 1
<211> LENGTH: 25
<212> TYPE: DNA
<213> ORGANISM: Artificial Sequence
<220> FEATURE:
<223> OTHER INFORMATION: synthesized

<400> SEQUENCE: 1
atagcttaac gcgtatgaca tcgca                                          25

<210> SEQ ID NO 2
<211> LENGTH: 25
<212> TYPE: DNA
<213> ORGANISM: Artificial Sequence
<220> FEATURE:
<223> OTHER INFORMATION: synthesized

<400> SEQUENCE: 2
gtgcgatgtc atacgcgtta agcta                                          25

<210> SEQ ID NO 3
<211> LENGTH: 25
<212> TYPE: DNA
<213> ORGANISM: Artificial Sequence
<220> FEATURE:
<223> OTHER INFORMATION: synthesized

<400> SEQUENCE: 3
atacaagctt cagacagttg tggtg                                          25

<210> SEQ ID NO 4
<211> LENGTH: 25
<212> TYPE: DNA
<213> ORGANISM: Artificial Sequence
<220> FEATURE:
<223> OTHER INFORMATION: synthesized

<400> SEQUENCE: 4
gcaccacaac tgtctgaagc ttgta                                          25

<210> SEQ ID NO 5
<211> LENGTH: 25
<212> TYPE: DNA
<213> ORGANISM: Artificial Sequence
<220> FEATURE:
<223> OTHER INFORMATION: synthesized

<400> SEQUENCE: 5
```

-continued

```
aatgtcatgg ttgtgacgtg catac                                              25

<210> SEQ ID NO 6
<211> LENGTH: 25
<212> TYPE: DNA
<213> ORGANISM: Artificial Sequence
<220> FEATURE:
<223> OTHER INFORMATION: synthesized

<400> SEQUENCE: 6
ggtatgcacg tcacaaccat gacat                                              25

<210> SEQ ID NO 7
<211> LENGTH: 25
<212> TYPE: DNA
<213> ORGANISM: Artificial Sequence
<220> FEATURE:
<223> OTHER INFORMATION: synthesized

<400> SEQUENCE: 7
atagcttgag accattacgt acggt                                              25

<210> SEQ ID NO 8
<211> LENGTH: 25
<212> TYPE: DNA
<213> ORGANISM: Artificial Sequence
<220> FEATURE:
<223> OTHER INFORMATION: synthesized

<400> SEQUENCE: 8
gaccgtacgt aatggtctca agcta                                              25

<210> SEQ ID NO 9
<211> LENGTH: 25
<212> TYPE: DNA
<213> ORGANISM: Artificial Sequence
<220> FEATURE:
<223> OTHER INFORMATION: synthesized

<400> SEQUENCE: 9
atagctaacc aacaccacta gagct                                              25

<210> SEQ ID NO 10
<211> LENGTH: 25
<212> TYPE: DNA
<213> ORGANISM: Artificial Sequence
<220> FEATURE:
<223> OTHER INFORMATION: synthesized

<400> SEQUENCE: 10
gagctctagt ggtgttggtt agcta                                              25

<210> SEQ ID NO 11
<211> LENGTH: 25
<212> TYPE: DNA
<213> ORGANISM: Artificial Sequence
<220> FEATURE:
<223> OTHER INFORMATION: synthesized

<400> SEQUENCE: 11
atagctaatc cggaacttgt ggtgt                                              25

<210> SEQ ID NO 12
<211> LENGTH: 25
<212> TYPE: DNA
```

```
<213> ORGANISM: Artificial Sequence
<220> FEATURE:
<223> OTHER INFORMATION: synthesized

<400> SEQUENCE: 12
gacaccacaa gttccggatt agcta                                           25

<210> SEQ ID NO 13
<211> LENGTH: 25
<212> TYPE: DNA
<213> ORGANISM: Artificial Sequence
<220> FEATURE:
<223> OTHER INFORMATION: synthesized

<400> SEQUENCE: 13
atacgattgg atcctagtac ggtag                                           25

<210> SEQ ID NO 14
<211> LENGTH: 25
<212> TYPE: DNA
<213> ORGANISM: Artificial Sequence
<220> FEATURE:
<223> OTHER INFORMATION: synthesized

<400> SEQUENCE: 14
gctaccgtac taggatccaa tcgta                                           25

<210> SEQ ID NO 15
<211> LENGTH: 8
<212> TYPE: DNA
<213> ORGANISM: Artificial Sequence
<220> FEATURE:
<223> OTHER INFORMATION: synthesized

<400> SEQUENCE: 15 ctcattcc                                                               8

<210> SEQ ID NO 16
<211> LENGTH: 9
<212> TYPE: DNA
<213> ORGANISM: Artificial Sequence
<220> FEATURE:
<223> OTHER INFORMATION: synthesized

<400> SEQUENCE: 16 tggaatgag                                                              9

<210> SEQ ID NO 17
<211> LENGTH: 8
<212> TYPE: DNA
<213> ORGANISM: Artificial Sequence
<220> FEATURE:
<223> OTHER INFORMATION: synthesized

<400> SEQUENCE: 17 aattcgcg                                                               8

<210> SEQ ID NO 18
<211> LENGTH: 9
<212> TYPE: DNA
<213> ORGANISM: Artificial Sequence
<220> FEATURE:
<223> OTHER INFORMATION: synthesized

<400> SEQUENCE: 18 tcgcgaatt                                                              9
```

```
<210> SEQ ID NO 19
<211> LENGTH: 9
<212> TYPE: DNA
<213> ORGANISM: Artificial Sequence
<220> FEATURE:
<223> OTHER INFORMATION: synthesized

<400> SEQUENCE: 19 caattcgcg                                                                 9

<210> SEQ ID NO 20
<211> LENGTH: 8
<212> TYPE: DNA
<213> ORGANISM: Artificial Sequence
<220> FEATURE:
<223> OTHER INFORMATION: synthesized

<400> SEQUENCE: 20 cgcgaatt                                                                  8

<210> SEQ ID NO 21
<211> LENGTH: 8
<212> TYPE: DNA
<213> ORGANISM: Artificial Sequence
<220> FEATURE:
<223> OTHER INFORMATION: synthesized

<400> SEQUENCE: 21 cctttagc                                                                  8

<210> SEQ ID NO 22
<211> LENGTH: 9
<212> TYPE: DNA
<213> ORGANISM: Artificial Sequence
<220> FEATURE:
<223> OTHER INFORMATION: synthesized

<400> SEQUENCE: 22 tgctaaagg                                                                 9

<210> SEQ ID NO 23
<211> LENGTH: 9
<212> TYPE: DNA
<213> ORGANISM: Artificial Sequence
<220> FEATURE:
<223> OTHER INFORMATION: synthesized

<400> SEQUENCE: 23 ccctttagc                                                                 9

<210> SEQ ID NO 24
<211> LENGTH: 8
<212> TYPE: DNA
<213> ORGANISM: Artificial Sequence
<220> FEATURE:
<223> OTHER INFORMATION: synthesized

<400> SEQUENCE: 24 gctaaagg                                                                  8

<210> SEQ ID NO 25
<211> LENGTH: 8
<212> TYPE: DNA
<213> ORGANISM: Artificial Sequence
<220> FEATURE:
```

```
<223> OTHER INFORMATION: synthesized

<400> SEQUENCE: 25 acagagac                                                                    8

<210> SEQ ID NO 26
<211> LENGTH: 9
<212> TYPE: DNA
<213> ORGANISM: Artificial Sequence
<220> FEATURE:
<223> OTHER INFORMATION: synthesized

<400> SEQUENCE: 26 tgtctctgt                                                                   9

<210> SEQ ID NO 27
<211> LENGTH: 9
<212> TYPE: DNA
<213> ORGANISM: Artificial Sequence
<220> FEATURE:
<223> OTHER INFORMATION: synthesized

<400> SEQUENCE: 27 cacagagac                                                                   9

<210> SEQ ID NO 28
<211> LENGTH: 8
<212> TYPE: DNA
<213> ORGANISM: Artificial Sequence
<220> FEATURE:
<223> OTHER INFORMATION: synthesized

<400> SEQUENCE: 28 gtctctgt                                                                    8

<210> SEQ ID NO 29
<211> LENGTH: 8
<212> TYPE: DNA
<213> ORGANISM: Artificial Sequence
<220> FEATURE:
<223> OTHER INFORMATION: synthesized

<400> SEQUENCE: 29 ccgtcata                                                                    8

<210> SEQ ID NO 30
<211> LENGTH: 9
<212> TYPE: DNA
<213> ORGANISM: Artificial Sequence
<220> FEATURE:
<223> OTHER INFORMATION: synthesized

<400> SEQUENCE: 30 ttatgacgg                                                                   9

<210> SEQ ID NO 31
<211> LENGTH: 9
<212> TYPE: DNA
<213> ORGANISM: Artificial Sequence
<220> FEATURE:
<223> OTHER INFORMATION: synthesized

<400> SEQUENCE: 31 cccgtcata                                                                   9
```

```
<210> SEQ ID NO 32
<211> LENGTH: 8
<212> TYPE: DNA
<213> ORGANISM: Artificial Sequence
<220> FEATURE:
<223> OTHER INFORMATION: synthesized

<400> SEQUENCE: 32 tatgacgg                                                              8

<210> SEQ ID NO 33
<211> LENGTH: 8
<212> TYPE: DNA
<213> ORGANISM: Artificial Sequence
<220> FEATURE:
<223> OTHER INFORMATION: synthesized

<400> SEQUENCE: 33 ggatctac                                                              8

<210> SEQ ID NO 34
<211> LENGTH: 9
<212> TYPE: DNA
<213> ORGANISM: Artificial Sequence
<220> FEATURE:
<223> OTHER INFORMATION: synthesized

<400> SEQUENCE: 34 tgtagatcc                                                             9

<210> SEQ ID NO 35
<211> LENGTH: 9
<212> TYPE: DNA
<213> ORGANISM: Artificial Sequence
<220> FEATURE:
<223> OTHER INFORMATION: synthesized

<400> SEQUENCE: 35 cggatctac                                                             9

<210> SEQ ID NO 36
<211> LENGTH: 8
<212> TYPE: DNA
<213> ORGANISM: Artificial Sequence
<220> FEATURE:
<223> OTHER INFORMATION: synthesized

<400> SEQUENCE: 36 gtagatcc                                                              8

<210> SEQ ID NO 37
<211> LENGTH: 8
<212> TYPE: DNA
<213> ORGANISM: Artificial Sequence
<220> FEATURE:
<223> OTHER INFORMATION: synthesized

<400> SEQUENCE: 37 gttgcatc                                                              8

<210> SEQ ID NO 38
<211> LENGTH: 9
<212> TYPE: DNA
<213> ORGANISM: Artificial Sequence
<220> FEATURE:
<223> OTHER INFORMATION: synthesized
```

```
<400> SEQUENCE: 38 tgatgcaac                                                             9

<210> SEQ ID NO 39
<211> LENGTH: 9
<212> TYPE: DNA
<213> ORGANISM: Artificial Sequence
<220> FEATURE:
<223> OTHER INFORMATION: synthesized

<400> SEQUENCE: 39 cgttgcatc                                                             9

<210> SEQ ID NO 40
<211> LENGTH: 8
<212> TYPE: DNA
<213> ORGANISM: Artificial Sequence
<220> FEATURE:
<223> OTHER INFORMATION: synthesized

<400> SEQUENCE: 40 gatgcaac                                                              8

<210> SEQ ID NO 41
<211> LENGTH: 9
<212> TYPE: DNA
<213> ORGANISM: Artificial Sequence
<220> FEATURE:
<223> OTHER INFORMATION: synthesized

<400> SEQUENCE: 41 catcgggaa                                                             9

<210> SEQ ID NO 42
<211> LENGTH: 8
<212> TYPE: DNA
<213> ORGANISM: Artificial Sequence
<220> FEATURE:
<223> OTHER INFORMATION: synthesized

<400> SEQUENCE: 42 ttcccgat                                                              8

<210> SEQ ID NO 43
<211> LENGTH: 59
<212> TYPE: DNA
<213> ORGANISM: Artificial Sequence
<220> FEATURE:
<223> OTHER INFORMATION: synthesized

<400> SEQUENCE: 43
gcgcgcttgg ttcagacgtg agaagtgatg cacagtagct taacgcgtat gacatcgca    59

<210> SEQ ID NO 44
<211> LENGTH: 27
<212> TYPE: DNA
<213> ORGANISM: Artificial Sequence
<220> FEATURE:
<223> OTHER INFORMATION: synthesized

<400> SEQUENCE: 44
gcgcgctacc gtactaggat ccaatcg                                        27
```